United States Patent [19]

Gardner et al.

[11] Patent Number: 4,827,031

[45] Date of Patent: May 2, 1989

[54] PROCESS FOR PREPARING AMINES FROM OLEFINS WITH AMMONIUM HALIDE CATALYSTS

[75] Inventors: David M. Gardner, Worcester; Paul J. McElligott, Abington; Roger T. Clark, Chester, all of Pa.

[73] Assignee: Pennwalt Corporation, Philadelphia, Pa.

[21] Appl. No.: 51,965

[22] Filed: May 19, 1987

Related U.S. Application Data

[63] Continuation of Ser. No. 836,874, Mar. 6, 1986, abandoned, which is a continuation-in-part of Ser. No. 724,737, Apr. 18, 1985, abandoned.

[51] Int. Cl.$^4$ .............................................. C07C 85/18
[52] U.S. Cl. ..................................... 564/485; 544/106; 546/184; 548/579; 564/408; 564/445
[58] Field of Search ....................... 564/408, 445, 485; 544/106; 546/184; 548/579

[56] References Cited

U.S. PATENT DOCUMENTS

| | | | |
|---|---|---|---|
| 3,412,158 | 11/1968 | McClain | 564/485 |
| 4,083,874 | 4/1978 | McConaghy et al. | 564/485 |
| 4,454,321 | 6/1984 | Gardner et al. | 564/485 |

FOREIGN PATENT DOCUMENTS 520073  12/1955  Canada ................................. 564/485

*Primary Examiner*—Richard L. Raymond

[57] ABSTRACT

The process for preparing aliphatic and aromatic amines by reacting an olefin with either ammonia, a primary amine, or a secondary amine at elevated temperature in the presence of an ammonium halide catalyst, preferably a catalyst-promoter combination, is disclosed herein.

18 Claims, No Drawings

PROCESS FOR PREPARING AMINES FROM OLEFINS WITH AMMONIUM HALIDE CATALYSTS

This is a continuation of co-pending application Ser. No. 836,874, filed on Mar. 6, 1986, now abandoned, which in turn is a continuation-in-part of copending application Ser. No. 724,737, filed Apr. 18, 1985, now abandoned.

BACKGROUND OF THE INVENTION

This invention relates to a process for producing amines by the reaction, at elevated temperature, of ammonia or a primary or secondary amine with an olefin in the presence of an ammonium halide-containing catalyst. Preferably, the catalyst is used in conjunction with a specified transition metal promoter.

PRIOR ART

The reaction of ammonia with olefins in the vapor phase over a variety of catalysts including certain metal salts and oxides and mixtures of metal salts and oxides deposited on inert, porous supports is known in the art. The products of such reaction are reportedly mixtures of amines, nitriles, polyamines, polyolefins and degradation products. The low selectivity to amines is the primary reason this technology has never been commercialized.

In U.S. Pat. No. 4,483,757 issued Nov. 20, 1984, there is disclosed a liquid phase, photochemical process of reacting an olefin with ammonia or a primary or secondary amine in the presence of ammonium iodide or ammonium bromide catalyst. The reaction is carried out under the influence of light having spectral emissions in excess of 160 nm. and at a temperature ranging from the freezing temperature of the reactants up to about 40° C.

STATEMENT OF THE INVENTION

This invention is a process for preparing amines comprising reacting ammonia or a primary or secondary amine with an aliphatic monoolefin having from 2 to 8 carbon atoms at a temperature ranging from about 170° to about 450° C., at a pressure of from about atmospheric up to about 8500 psi and in the presence of an ammonium halide-containing catalyst. The foregoing process is further improved by the incorporation of certain non-catalytic transition metal compounds (promoters) as a part of the catalyst system to thereby significantly increase catalyst activity.

DETAILED DISCUSSION OF THE INVENTION

This invention is directed to an improved process for the preparation of aliphatic and aromatic amines which comprises reacting an aliphatic monoolefin having from 2 to 8 carbon atoms with ammonia or a primary or secondary amine. The reaction is carried out at a temperature and pressure sufficient to effect rapid formation of amine, but mild enough to minimize formation of olefin polymer, polyamines, and other undesirable side products.

Examples of the monoolefins suitable for producing amines by this process are ethylene, propylene, 1-butene, isobutylene, 1-pentene, 2-pentene, 2-methyl-2-butene, 1-hexene, 2-hexene, 3-hexene, 3-methyl-1-pentene, 1-heptene, 2-heptene, 1-octene, 2-octene, and 3-ethyl-2-hexene. Monoolefins having from 2 to 4 carbon atoms are preferred.

Specific examples of the N-H containing reactants which are used in this process include ammonia, methylamine, dimethylamine, ethylamine, diethylamine, n-propylamine, di(n-propyl)amine, isopropylamine, di(isopropyl)amine, n-butylamine, di(n-butyl)amine isobutylamine, di(isobutyl)amine, the pentyl and higher alkylamines; cycloaliphatic amines eg., cyclohexylamine; aromatic amines, eg., aniline; the N-alkylanilines, diphenylamine, the naphthylamines, and the toluidines; heterocyclic amines, eg., pyrrolidine, morpholine, and piperidine; substituted amines, eg., alkanolamines; and polyamines, eg., ethylenediamine and 1,6-hexanediamine. The preferred N-H containing reactant, because of its commercial significance, is ammonia.

In the process of this invention, ammonia or an amine is reacted with an olefin at temperatures over a range of about 170° to about 450° C. The preferred temperature range is about 250° to about 350° C. Lower temperatures result in lower conversion and higher temperatures result in lower selectivity to the desired amine product.

Pressures in the range of atmospheric to above 8,500 psig are useful for carrying out this invention, however, pressures in excess of 8,000 psig tend to promote polymerization of the olefin. Pressures in the range of about 1,200 psig to about 4,000 psig are preferred.

The molar ratio of ammonia or amine to olefin can be from about 20:1 to 0.2:1 with the preferred range of from 4:1 to 1:1.

An important factor in achieving the desired results of high amine selectivity and low byproduct formation in this process in the use of ammonium halide-containing catalysts. The catalyst may be ammonium fluoride, ammonium chloride, ammonium bromide, ammonium iodide or an alkyl- or aryl-substituted ammonium halide such as ethylammonium iodide. In addition, the ammonium halide-containing compositions employed as catalysts herein include halide compounds which react with ammonia under the process conditions disclosed to form the corresponding ammonium halide which will in turn catalyze the reaction to form amines from olefins.

Examples of such halide compounds are alkyl halides and reactive metal halides, e.g., zinc chloride, cobalt (II) chloride, chromium (III) chloride, copper (II) chloride, copper (II) iodide, boron fluoride, ammonium fluoroborate, ammonium hexafluorophosphate, ammonium hexafluorogermanate, tin (II) chloride, ferric chloride, and silicon halides. The preferred catalysts of this invention are ammonium iodide, ammonium bromide, and ammonium chloride. The halide catalysts can be used individually or in combinations with each other to improve conversions and yields.

The foregoing halides can be advantageously used in this process dissolved in a suitable solvent or mounted or deposited on a suitable solid, porous, inert catalyst support. For example, such supports include alumina, silica-alumina, silica, carbon, calcium aluminate, kieselguhr, titania, zirconia, magnesia, silica-magnesia, various clays and refractory materials. Examples of catalyst solvents include water, ethanol, ethylene glycol, t-butylalcohol, and various amines, olefins and hydrocarbons.

For homogeneous liquid phase catalyst systems, where the halide is dissolved in a solvet, the halide can be used in any catalytically effective amount with respect to the amine or ammonia reactant; the preferred amount ranging from at least 0.01 mole/mole of amine or ammonia up to the limit of solubility of the halide in a reaction media. Reaction times depend on the catalyst concentration, reaction conditions and on the reactants, but generally fall in a range of from 1 minute to 5 hours.

For a continuous heterogenous vapor phase catalyst, where the halide is mounted or deposited on a solid support, the reaction time is defined in terms of the gas hourly space velocity (GHSV) which has units of, volume of gas per volume of catalyst in unit time, i.e., (cc gas at STP)/(cc catalyst) (hours$^{-1}$). STP means standard temperature (25° C.) and pressure (1 atm.). The gas hourly space velocity can be from about 300 to 15,000 hr$^{-1}$. As the space velocity is increased toward the upper end of the range, particularly above 5,000 hr,$^{-1}$ conversion falls off. On the other hand, as the space velocity approaches the lower level of 300 hr$^{-1}$, the reaction mixture approaches equilibrium hence the production rate falls to zero. Where the olefin is isobutylene, typical conversions of from about 14% to 22% are achieved at space velocities of about 2,300 to 550 hr$^{-1}$.

The non-catalytic transition metal promoters which will significantly increase the catalytic activity of the ammonium halide catalyst include the transition metal halides and ammonium salts of oxyacids. Examples of these compounds include chromium chloride ($CrCl_3$), chromium iodide ($CrI_3$), copper iodide (CuI), zinc chloride ($ZnCl_2$), ammonium phosphomolybdate [$(NH_4)_3PO_4.12MoO_3.H_2O$], ammonium vanadate ($NH_4VO_3$), sodium stannate ($Na_2SnO_3$) and cobalt chloride hexahydrate ($CoCl_2.6H_2O$).

The promoter is used in admixture with the catalyst whereby there is intimate contact between the two substances. If the promoter is deposited on a solid support, it should be on the same support which bears the catalyst.

The promoter is used in any amount which will improve the performance of the ammonium halide catalyst in this process, the preferred amount of promoter ranging from about 1 to about 0.01 parts, more preferably from about 0.1 to 0.05 parts by weight of promoter per part by weight of active catalyst.

The preferred catalyst-promoter combination is ammonium iodide-chromium chloride.

In accordance with this process, the amination of the olefin with ammonia or an amine (primary or secondary) provides amines of the next level of substitution. Thus, ammonia yields principally primary amines, primary amines yield secondary amines and secondary amines yield tertiary amines. The general reaction for the process is illustrated by the following equation:

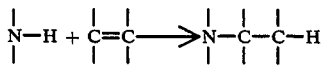

Two methods of carrying out this reaction have been investigated. In the first or static method, the catalyst, olefin, ammonia and solvent, if employed, are placed in an autoclave, and heated electrically. The reactant mixture is agitated (stirring or shaking) under autogenous pressure for a prescribed period of time. The autoclave is cooled and the products recovered. In the second or continuous method, the catalyst may be either neat or supported on an inert support, such as described above, and the reactants are passed over the catalyst at elevated temperatures and pressure using a suitably designed apparatus.

The following examples illustrate the preferred embodiments of this invention and are not intended to restrict its scope. Percentages are mole percents, temperatures are in degrees centigrade, and pressures are in pounds per square inch gauge (i.e., above atmospheric pressure). Conversions and yields given in these examples are based on the isolated products. Conversion is defined as the percentage of olefin charged to the reaction zone which has undergone reaction. Yield is defined as the percent of olefin reacted which has formed the indicated product(s). Major products were identified by gas chromatographic and mass-spectroscopic analytical methods and when necessary, were confirmed by distillation followed by infrared spectrophotometry and nuclear magnetic resonance spectroscopy. Those minor products which are not identified are assumed to have the same gas chromatographic response factor as the major amine product.

It has been observed when carrying out the process described herein, that in the absence of a catalyst or in the presence of an ineffective catalyst, that no amine products are formed.

EXAMPLE 1

A mixture of 19.3 g (1.1 moles) anhydrous ammonia, 14.8 g (0.53 mole) of ethylene, 14.5 g (0.10 mole) ammonium iodide and 81 g of water were charged to a 300 cm$^3$ stainless steel autoclave. The autoclave was heated to 330° C. and held there for five hours with agitation; the maximum system pressure was 2,800 psig. A total of 7.0 g of monoethylamine, 1.1 g of diethylamine, 0.02 g of triethylamine, and 1.1 g of ethyl alcohol were obtained, corresponding to an ethylene conversion of 43.9% and a combined ethylamines yield of 83.8% and ethyl alcohol yield of 11.0%. The balance consisted of approximately 0.33 g of a hydrocarbon oil.

EXAMPLE 2

A mixture of 34.1 g (2.0 moles) anhydrous ammonia, 28.0 g (1.0 mole) of ethylene and 14.5 g (0.10 mole) of ammonium iodide were charged to a 300 cm$^3$ stainless steel autoclave. The autoclave was heated to 368°–370° C. and held there for five hours with agitation; the maximum system pressure was 5,100 psig. A total of 4.2 g of monoethylamine, 0.1 g of diethylamine, and detectable quantities of triethylamine were obtained, corresponding to an ethylene conversion of 10.2% and a combined ethylamines yield of 92.2%. The balance consisted of approximately 0.2 g of a hydrocarbon oil.

EXAMPLE 3

A mixture of 8.9 g (0.52 mole) anhydrous ammonium, 7.5 g (0.27 mole) of ethylene and 14.5 g (0.10 moles) of ammonium iodide were charged to a 300 cm$^3$ stainless steel autoclave. The autoclave was heated to 380°–381° C. and held there for five hours with agitation; the maximum system pressure was 1,125 psig. A total of 0.46 g of monoethylamine and a trace of diethylamine were obtained, corresponding to an ethylene conversion of 4.0% and a combined ethylamines yield of 100%.

In Examples 4–12 following, the autoclave was heated to 350° C. and held there for five hours with continuous agitation of the reactants unless specified otherwise.

EXAMPLE 4

A mixture of 34.1 g (2.0 moles) anhydrous ammonia, 28.0 g (1.0 mole) of ethylene and 5.4 g (0.10 mole) of ammonium chloride were charged to a 300 cm$^3$ stainless steel autoclave. The maximum system pressure was 5,100 psig. A total of 0.73 g of monoethylamine and trace amounts of diethylamine were obtained, corresponding to an ethylene conversion of 1.6% and an ethylamine yield of 100%.

EXAMPLE 5

A mixture of 34.1 g (2.0 moles) anhydrous ammonia, 28.0 g (1.0 mole) of ethylene and 13.2 g (0.13 mole) of ammonium bromide were charged to a 300 cm$^3$ stainless steel autoclave. The maximum system pressure was 6,000 psig. A total of 0.2 g of monoethylamine and 0.2 g of a hydrocarbon oil were obtained, corresponding to an ethylene conversion of 1.2% and an ethylamine yield of 38%.

EXAMPLE 6

A mixture of 34.1 g (2.0 moles) anhydrous ammonia, 28.0 g (1.0 mole) of ethylene and 3.7 g (0.10 mole) of ammonium fluoride were charged to a 300 cm$^3$ stainless steel autoclave. The maximum system pressure was 4,600 psig. Trace amounts of monoethylamine were obtained.

EXAMPLE 7

A mixture of 18.5 g (1.1 moles) of anhydrous ammonia, 27.9 g (0.5 mole) of isobutylene, 78.7 g of water and 43.6 g (0.10 mole) of ammonium iodide were charged to a 300 cm$^3$ stainless steel autoclave. The autoclave was heated to 315° C. and held there for two hours with agitation; the maximum system pressure was 2,900 psig. A total of 6.4 g of t-butylamine, 8.1 g of t-butyl alcohol and 0.3 g of a hydrocarbon oil were obtained, corresponding to an isobutylene conversion of 27.2% and a t-butylamine yield of 65%, t-butyl alcohol yield of 31% and oil yield of 3.9%.

EXAMPLE 8

A mixture of 18.1 g (1.1 moles) of anhydrous ammonia, 27.5 g (0.5 mole) of cis, trans-2-butenes, 79.1 g of water and 43.5 g (0.10 mole) of ammonium iodide were charged to a 300 cm$^3$ stainless steel autoclave. The autoclave was heated to 335° C. and held there for five hours with agitation; the maximum system pressure was 3,100 psig. A total of 3.3 g of mono-sec-butylamine, 0.01 g of di-sec-butylamine, 0.42 g of mono-n-butylamine, 1.29 g of sec-butyl alcohol, 0.06 g n-butyl alcohol, 0.35 g methylethylketone and 0.93 g of a hydrocarbon oil were obtained, corresponding to a 2-butene conversion of 19.9%, an amines yield of 52.1%, an alcohol yield of 25.9%, MEK yield of 5.0% and an oil yield of 17.0%.

EXAMPLE 9

A mixture of 17.0 g (1.0 mole) anhydrous ammonia, 28.0 g (0.5 mole) of isobutylene and 16.0 g (0.3 mole) ammonium chloride were charged to a 300 cm$^3$ stainless steel autoclave. The autoclave was heated to 315° C. and held there for 2 hours with agitation. The maximum system pressure was 2,900 psig. A total of 0.82 g of t-butylamine was obtained, corresponding to an isobutylene conversion of 2.2%, a t-butylamine yield of 43% and a hydrocarbon oil yield of 57%.

EXAMPLE 10

A mixture of 17.0 g (1.0 mole) of anhydrous ammonia, 21.0 g (0.5 mole) of propylene and 16.0 g (0.3 mole) of ammonium chloride were charged to a 300 cm$^3$ stainless steel autoclave. The autoclave was heated to 335° C. and held there for with agitation. The maximum system pressure was 2,800 psig. A total of 2.6 g of monoisopropylamine and 0.54 g of diisopropylamine was obtained, corresponding to a propylene conversion of 10.9%, a combined isopropyl- and diisopropylamine yield of 62.5% and a hydrocarbon oil yield of 89.1%.

EXAMPLE 11

A mixture of 16.9 g (1.0 mole) of anhydrous ammonia, 21.1 g (0.5 mole) of propylene, 50.0 g water and 43.5 g (0.3 mole) of ammonium iodide were charged to a 300 cm$^3$ stainless steel autoclave. The autoclave was heated to 335° C. and held there with agitation. A total of 5.8 g of monoisopropylamine, 0.13 g of diisopropylamine, 1.6 g isopropyl alcohol, 0.20 g of n-propyl alcohol and 0.6 g of a hydrocarbon oil were obtained, corresponding to a propylene conversion of 29% and a combined isopropylamines yield of 69%, propyl alcohols yield of 21% and oil yield of 10%.

EXAMPLE 12

A mixture of 45.1 g (0.5 mole) of dimethylamine, 14.0 g (0.5 mole) of ethylene and 16.0 g (0.3 mole) of ammonium chloride were charged to a 300 cm$^3$ stainless steel autoclave. The autoclave was heated to 325° C. and held there with agitation. The maximum system pressure was 3,400 psig. A total of 2.18 g of dimethylethylamine and 2.35 g of diethylmethylamine were obtained, corresponding to an ethylene conversion of 30.1% and a combined dimethylethyl-amine and diethylmethylamine yield of 55.6%.

EXAMPLE 13

A continuous reactor system was used consisting of a reactor 12-inches long by 0.625-inches I.D. A thermowell of 0.25-inches O.D. was mounted coaxially inside the reactor. The catalyst was held in the reactor by plugs of glass wool on either side of the catalyst, and the reactor tube was electrically heated.

The catalyst employed was prepared by dissolving 0.1 moles of ammonium iodide in 1.8 moles of methanol and injecting the solution into an evacuated flask containing 25 grams of carbon (Darco LI-100). The carbon was transferred in air into an evacuated desiccator where the methanol was vaporized at 70° C. under 0.1 mm Hg. This catalyst (36.7% NH$_4$I on carbon, based on the weight of the combined catalyst system) was loaded into the reactor described above and dried under a nitrogen purge; first, at 70° C. for one hour then at 390° C. for an additional hour.

Ethylene and anhydrous liquid ammonia were fed from individual tanks by metering valves through flow meters and then mixed prior to vaporization in a coil of tubing immersed in hot silicon-oil maintained at 200° C. The molar feed ratio of ammonia and ethylene was 6.7 to 1.0. After seven hours of continuous running at 350° C. and 350 psig of system pressure at a throughput of 14,000 GHSV, the total product was analyzed and found to contain monoethylamine in 98% yield and at a 7.7% conversion of ethylene. The product stream was trapped in a 3-liter cylinder chilled to −78° C. and analyzed gas chromatographically.

For comparison purposes, carbon (Darco LI-100; 25 g) was charged untreated (no ammonium iodide), in place of the above-described catalyst system, into the reactor system described above. The mixed ammonia and ethylene feed was vaporized and passed through the reactor tube maintained at 320° C. and a pressure of 350 psig and at 14,000 GHSV. The resulting product contained only ammonia and ethylene and no amine, demonstrating that no amine is formed in the absence of ammonium halide.

Additionally, for comparison purposes, pure carbon (Westvaco; type-WVB) was charged (12.2 g), in place of the catalyst system, into the reactor described above, and the $NH_3/C_2H_4$ gas mixture at a mole ratio of 11.8 to 1 was passed through the carbon bed in the reactor at a velocity of 1550 GHSV. The reactor was maintained at 200 psig and 190° C. No amine product was found.

EXAMPLE 14

Unsupported, solid, 100% ammonium iodide (25 g) (12–18 mesh) was loaded as a catalyst into the reactor system described in Example 13.

A gaseous mixture of ammonia and ethylene (molar ratio 11.8:1.0) was passed over and through the salt-catalyst at 176° C. and 170 psig of system pressure at a space velocity of 1,550 GHSV. The product gases were condensed in an evacuated cylinder chilled to −78° C. The product was analyzed by gas chromatography. The resulting product contained monoethylamine formed at an ethylene conversion of 40% in 99+% yield.

EXAMPLE 15

20 grams of a catalyst consisting of 28.5% (based on weight of catalyst system) $NH_4I$ on carbon (Westvaco; type-WVB) was placed into a reactor as described in Example 13 where it was heated and dried at 70° C. with a $N_2$ stream passing over the catalyst for one hour. This was followed by increasing the temperature to 290° C. and maintaining it there for one hour.

A liquid mixture of ammonia containing 1% propylene (mole ratio 256:1/$NH_3$:$C_3H_6$) was vaporized at 250° C. and the hot gases were passed through the catalyst bed at 2000 GHSV. The reactor was maintained at 300° C. and 190 psig. The product mixture contained propylamines in the molar ratio of 2.5:1.0 (n-propyl to isopropyl). The amines were produced in 2% conversion of propylene and a 80+% yield.

EXAMPLE 16

A catalyst as described in Example 13 was placed in a reactor as described in Example 13 where it was heated and dried at 70° C. with a nitrogen purge for one hour and at 290° C. for an additional hour.

A liquid mixture of ammonia containing 5 weight percent of dissolved ethylene (mole ratio 31.3:1.0/$NH_3$:$C_2H_4$) was vaporized and the reactant gas mixture at 1550 GHSV was passed through the catalyst bed maintained at 300° C. and 175 psig pressure. The product mixture contained only monoethylamine and unconverted ammonia and ethylene. The amine was formed at a 2% conversion of ethylene and a 99+% yield.

The following Example is specific to the incorporation of a promoter (i.e., $CrCl_3$) in a silica-supported $NH_4I$ vapor phase catalyst.

EXAMPLE 17

The reactor used for this work consisted of a 10 ft. coil of 316-SS tube 0.032" wall thickness. The catalyst (60–80 mesh) was packed into the tube coil by suction and both ends were plugged with glass wool. The coil was heated by immersing it in a eutectic salt bath maintained at reaction temperature.

The catalyst employed was prepared by vacuum impregnation of Armak Silica (Si-5P) with 29% ammonium iodide/1% chromium chloride based on the weight of the total catalyst system (active catalyst, promoter and support), followed by drying under nitrogen at 100° C.

The reaction product was sampled by scrubbing the product stream with water (10° C.–0° C.) and condensing the water insoluble fraction in a dry-ice/acetone trap. No non-condensables were generated. The products were analyzed by gas chromatography.

A 1.5/1 molar mixture of ammonia/isobutylene was fed at a rate of 2 grams/minute (GHSV=2,255 $hr^{-1}$) to the above-described reactor containing 40 $cm^3$ of catalyst maintained at 275° C. and a pressure of 3,800 psi over a period of 3.53 hours; 425 grams of reactants were passed over the catalyst. A total of 53.0 g of t-butylamine was obtained, corresponding to an isobutylene conversion of 13.8% and a t-butylamine yield of 100%. No coking or deactivation of the catalyst was noted and no hydrocarbon oil was formed.

We claim:

1. A process for producing amines consisting essentially of reacting ammonia or a primary or secondary amine with an aliphatic monoolefin having from 2 to 8 carbon atoms at a temperature ranging from about 170° to about 450° C., at a pressure of from about atmospheric to about 8500 psig and in the presence of an ammonium halide-containing catalyst, and optionally in the presence of a promoter selected from the group consisting of a transition metal halide and an ammonium salt of an inorganic oxyacid, present in an amount to improve the activity of the catalyst.

2. The process of claim 1 wherein the reaction is continuous.

3. The process of claim 1 wherein the temperature ranges from about 250° to about 350° C. and the pressure ranges from about 1200 to about 4000 psig.

4. The process of claim 1 wherein said ammonium halide is ammonium iodide, ammonium bromide or ammonium chloride.

5. The process of claim 1 wherein said ammonium halide is mounted on an inert, porous support.

6. The process of claim 1 wherein said ammonium halide is dissolved or suspended in a solvent.

7. The process of claim 6 where the solvent is water.

8. The process of claim 5 wherein the temperature ranges from about 250° to about 350° C. and the pressure ranges from about 1200 to about 4000 psig.

9. The process of claim 8 wherein the reactants are ammonia or a primary or secondary alkylamine having from 1 to 4 carbon atoms and a monoolefin having from 2 to 4 carbon atoms.

10. The process of claim 9 wherein said ammonium halide is dissolved or suspended in a solvent.

11. The process of claim 10 wherein said solvent is water.

12. The process of claim 9 wherein said ammonium halide is mounted on an inert, porous support.

13. The process of claim 12 wherein said support is silica.

14. The process of claim 12 wherein the reaction is continuous.

15. The process of claim 13 wherein the reaction is continuous.

16. The process of claim 8 wherein the promoter is present in an amount of about 1 to about 0.01 parts by weight per part by weight of active catalyst.

17. The process of claim 16 wherein the promoter is mounted on an inert, porous support.

18. The process of claim 17 wherein the catalyst is ammonium iodide and the promoter is chromium chloride.

* * * * *

UNITED STATES PATENT AND TRADEMARK OFFICE
CERTIFICATE OF CORRECTION

PATENT NO.  : 4,827,031
DATED       : May 2, 1989
INVENTOR(S) : D. M. Gardner, P. J. McElligott, R. T. Clark It is certified that error appears in the above—identified patent and that said Letters Patent is hereby corrected as shown below:

Column 8, line 56, change "claim 5" to -- claim 4 --.

Signed and Sealed this

Ninth Day of January, 1990

*Attest:*

JEFFREY M. SAMUELS

*Attesting Officer*    *Acting Commissioner of Patents and Trademarks*